(12) United States Patent
Pekar et al.

(10) Patent No.: US 7,000,483 B2
(45) Date of Patent: Feb. 21, 2006

(54) INFLATABLE MANOMETERS

(75) Inventors: Robert W. Pekar, Florence, MA (US); Adam S. Epstein, Weston, MA (US); Scott R. Cadwallader, Northampton, MA (US)

(73) Assignee: Dielectrics Industries, Inc., Chicopee, MA (US)

( * ) Notice: Subject to any disclaimer, the term of this patent is extended or adjusted under 35 U.S.C. 154(b) by 64 days.

(21) Appl. No.: 10/769,946

(22) Filed: Feb. 2, 2004

(65) Prior Publication Data

US 2004/0255685 A1 Dec. 23, 2004

Related U.S. Application Data

(60) Provisional application No. 60/468,728, filed on May 7, 2003, provisional application No. 60/444,545, filed on Feb. 3, 2003.

(51) Int. Cl.
*G01L 7/20* (2006.01)
(52) U.S. Cl. ............................ 73/748; 73/700
(58) Field of Classification Search ........... 73/700–756
See application file for complete search history.

(56) References Cited

U.S. PATENT DOCUMENTS

| | | | | |
|---|---|---|---|---|
| 3,890,962 A | * | 6/1975 | Ramsey, III | 600/486 |
| 3,901,083 A | * | 8/1975 | Wallace | 73/715 |
| 4,090,503 A | * | 5/1978 | Speidel | 600/497 |
| 4,148,123 A | * | 4/1979 | Neubeck et al. | 29/407.08 |
| 4,203,128 A | * | 5/1980 | Guckel et al. | 331/156 |
| 4,217,784 A | * | 8/1980 | Neubeck et al. | 73/732 |
| 4,295,471 A | * | 10/1981 | Kaspari | 600/488 |
| 4,420,981 A | * | 12/1983 | Schoen | 73/756 |
| 4,785,669 A | * | 11/1988 | Benson et al. | 73/718 |
| 4,881,400 A | * | 11/1989 | Goodman et al. | 73/709 |
| 4,991,590 A | * | 2/1991 | Shi | 600/480 |
| 5,490,514 A | * | 2/1996 | Rosenberg | 600/487 |

* cited by examiner

*Primary Examiner*—Max Noori
*Assistant Examiner*—Jermaine Jenkins
(74) *Attorney, Agent, or Firm*—Cantor Colburn LLP

(57) ABSTRACT

An inflatable air cell pressure transducer. The air cell has a concavity formed therein. The concavity has two edges, wherein increased pressure within the air cell causes contraction of the concavity moving the two edges closer.

15 Claims, 6 Drawing Sheets

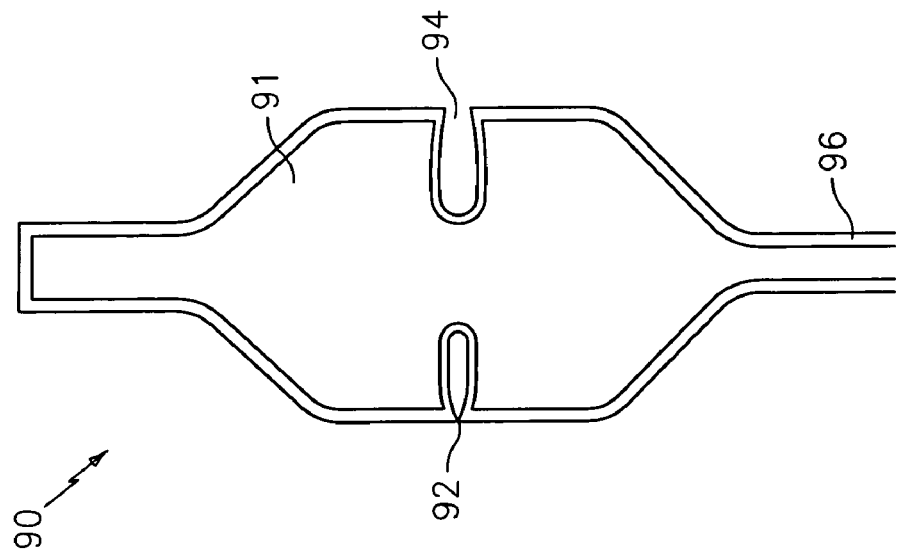
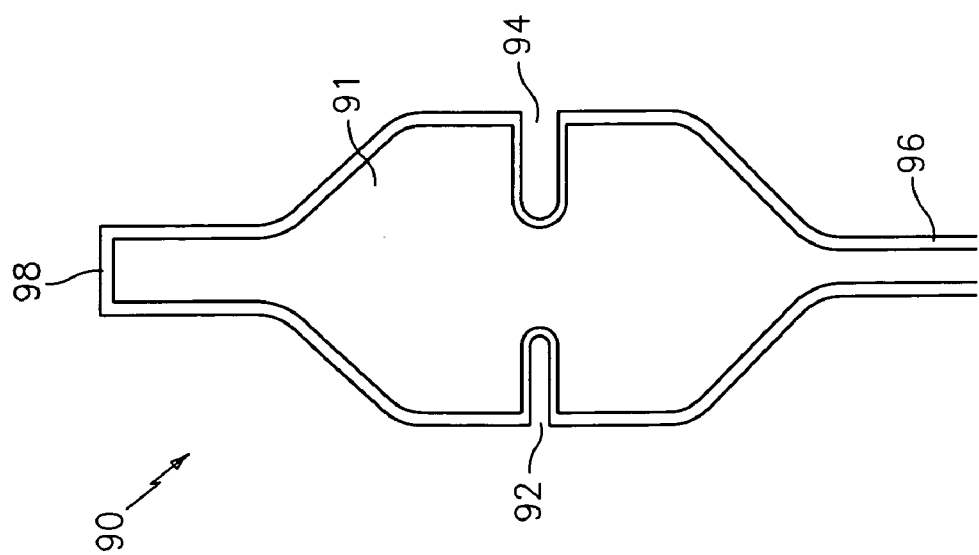

INFLATABLE MANOMETERS

CROSS-REFERENCE TO RELATED APPLICATIONS

This application claims the benefit of U.S. provisional patent application 60/444,545 filed Feb. 3, 2003, the entire contents of which are incorporated herein by reference, and claims the benefit of U.S. provisional patent application 60/468,728 filed May 7, 2003, the entire contents of which are incorporated herein by reference

BACKGROUND

The invention relates to inflatable manometers. Manometers are often used in medical procedures to monitor pressures in apparatus such as inflatable cuffs or manual resuscitators for a patient. For example, it is desirable to maintain the internal pressure of a tracheal tube cuff below 30 cmH$_2$O. Existing manometers are typically costly and can be a vehicle for disease transmission, rendering widespread use of such manometers prohibitive. Accordingly, there is a need in the art for a low cost, accurate manometer for medical applications (e.g., single-patient use disposable) and other applications.

BRIEF SUMMARY OF THE INVENTION

Embodiments of the invention include an inflatable manometer having an air cell. The air cell has a concavity formed therein. The concavity has two edges, or other geometric features, wherein increased pressure within the air cell causes contraction of the concavity moving the two edges closer.

BRIEF DESCRIPTION OF THE DRAWINGS

FIG. 8 depicts an inflatable manometer in an alternate embodiment of the invention.

FIG. 9 depicts the manometer of FIG. 8 as pressure increases.

DETAILED DESCRIPTION

Figure 1A:
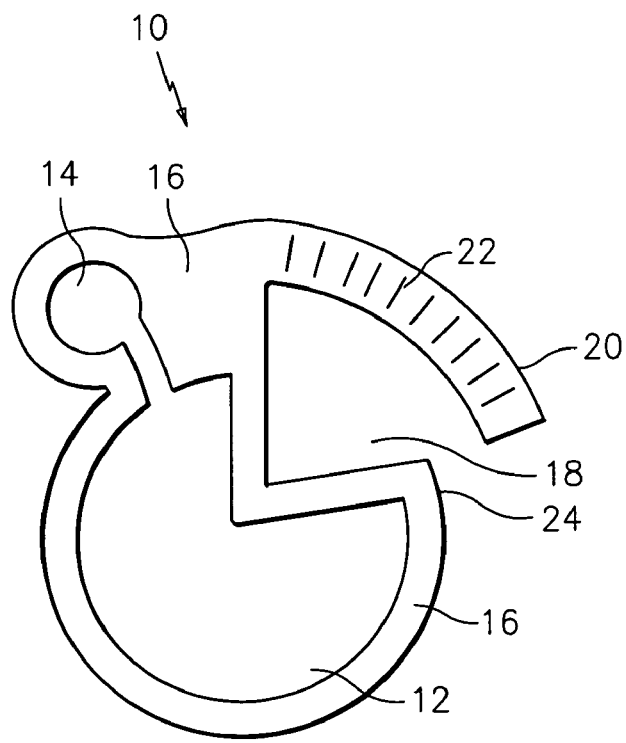
FIGS. 1A and 1B depict inflatable manometers in embodiments of the invention.
Figure 1B:
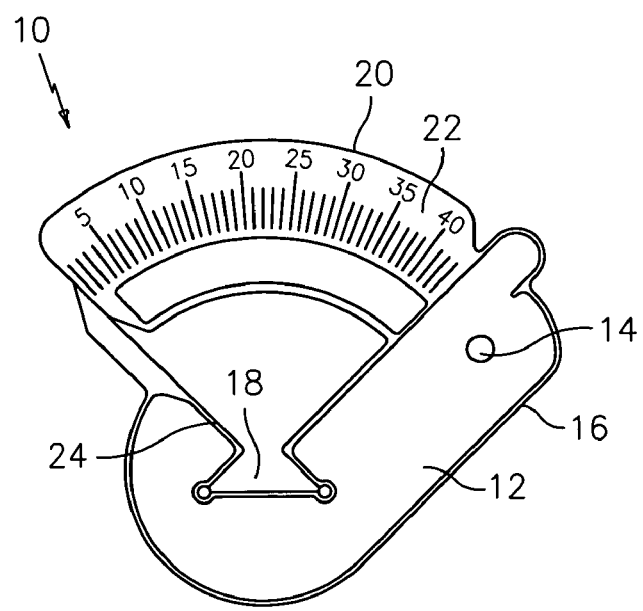

FIG. 1A depicts an inflatable manometer 10 in an embodiment of the invention. Manometer 10 includes an air cell 12 coupled to a fluid inlet 14. The manometer serves as an air cell pressure transducer that indicates pressure of the fluid which may be gas, liquid, etc. The air cell 12 is formed by two sheets of material sealed along seal 16. In one embodiment, the sheets of material are thermoplastic material and are sealed using known techniques such as heat sealing, ultrasonic welding, etc. The sheets of material are not limited to thermoplastic materials and may be implemented using any flexible material such as rubber, glued paper, etc. The air cell 12 is generally circular and includes a concavity 18 in the shape of a triangular wedge. It is understood that the air cell 12 and concavity 18 may have shapes other than those depicted in FIG. 1A. FIG. 1B depicts an alternate manometer similar to that shown in FIG. 1A, but having differently shaped concavity 18.

A scale 20 is also formed from the same sheets defining the air cell 12 and includes indicia 22 representative of pressure. The scale 20 and indicia 22 may be formed by molding the indicia 22 into thermoplastic sheets (e.g., heat stamping) or printing the indicia 22. The scale 20 is positioned proximate to edge 24 of concavity 18. The scale 20 can be designed for different real units of measure, e.g., PSI. In alternate embodiments, scale 20 is affixed to air cell 12 and moves relative to a stationary indicator.

Figure 2:
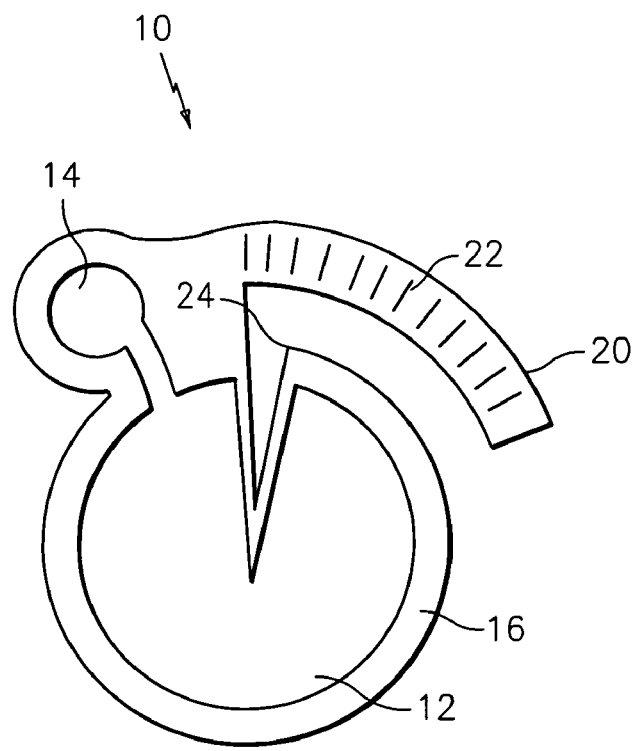
FIG. 2 depicts the manometer of FIG. 1A as pressure increases.

FIG. 2 depicts manometer 10 of FIG. 1A as pressure in air cell 12 increases. As the air cell 12 is inflated, the two edges that define the concavity 18 will contract towards each other in response to increasing internal fluid pressure. The pressure within the air cell 12 is represented by the position of edge 24 relative to scale 20. Thus, the size and shape of the air cell 12, concavity 18 and scale 20 are designed to provide an accurate indication of pressure.

Inlet 14 may be coupled to a tube in fluid communication with a chamber for which pressure monitoring is desired. Alternatively, manometer 10 may be secured on a sidewall of a chamber with inlet 14 in fluid communication with the chamber. The seal 16 around inlet 14 may be secured to the chamber wall (e.g., heat sealed to thermoplastic chamber) to provide an integrated manometer.

Figure 3:
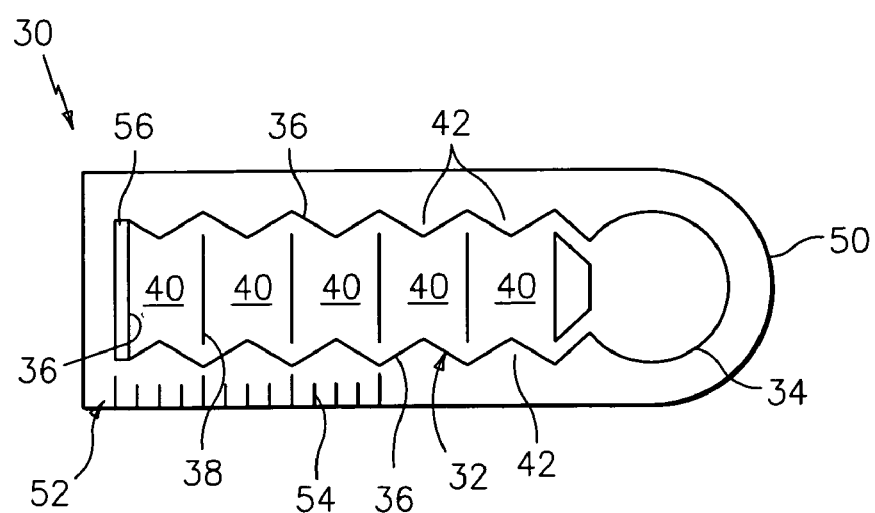
FIG. 3 depicts an inflatable manometer in an alternate embodiment of the invention.

FIG. 3 depicts an alternate manometer 30. Manometer 30 includes an air cell 32 and a fluid inlet 34. The manometer 30 indicates pressure of the fluid which may be gas, liquid, etc. The air cell 32 is formed by two sheets of material sealed along edges 36. Interior seals 38 define a number of rectangular sub-cells 40, each having a concavity 42 at each end defined by seals 36. In one embodiment, the sheets of material defining air cell 32 are thermoplastic material and are sealed using known techniques such as heat sealing, ultrasonic welding, etc. The sheets of material are not limited to thermoplastic materials and may be implemented using any flexible material such as rubber, glued paper, etc.

Air cell 32 and inlet 34 are positioned within a housing 50 having a first and second sheet sealed along the periphery encasing the air cell 32 and inlet 34. The first and second housing sheets may be thermoplastic material and are sealed using known techniques such as heat sealing, ultrasonic welding, etc. A scale 52 is also formed on the housing 50 and includes indicia 54 representative of pressure. The scale 52 and indicia 54 may be formed by molding the indicia 54 into thermoplastic sheets (e.g., heat stamping) or printing the indicia 54. The scale 52 is positioned proximate to a distal end 56 of air cell 32. The scale 52 can be designed for different real units of measure, e.g., PSI.

Figure 4:
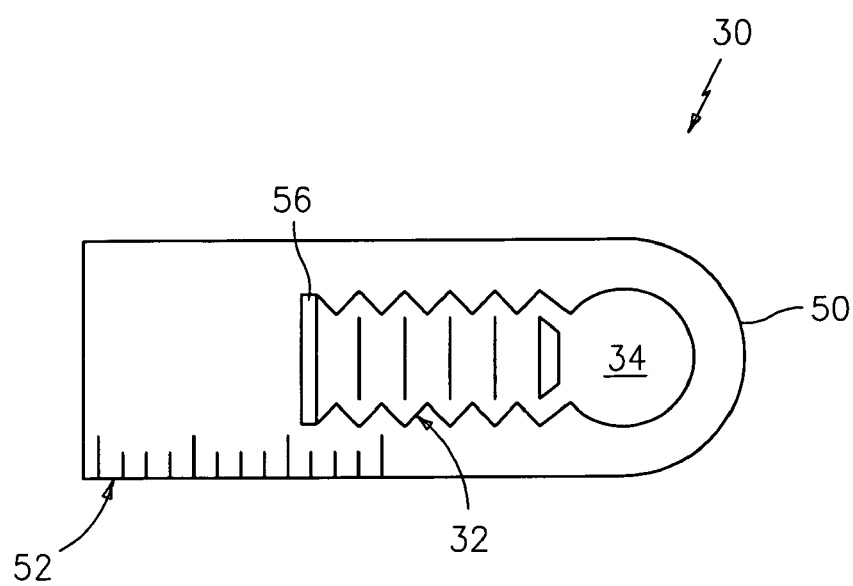
FIG. 4 depicts the manometer of FIG. 3 as pressure increases.

FIG. 4 depicts manometer 30 as pressure in air cell 32 increases. As the air cell 32 is inflated, rectangular sub-cells 40 expand into cylindrically shaped cells, thereby reducing the length of the air cell 32 in a linear direction. The pressure within the air cell 32 is represented by the position of distal end 56 relative to scale 52. The distal end 56 of the air cell 32 may be colored to more easily determine the position of the end of the air cell 32 relative to the scale 52. Thus, the size and shape of the air cell 32 and scale 52 are designed to provide an accurate indication of pressure.

Inlet 34 may be coupled to a tube in fluid communication with a chamber for which pressure monitoring is desired. Alternatively, manometer 30 may be secured on a sidewall of a chamber with inlet 34 in fluid communication with the chamber. The seal around inlet 34 may be secured to the chamber wall (e.g., heated sealed to thermoplastic chamber) to provide an integrated manometer.

Figure 5:
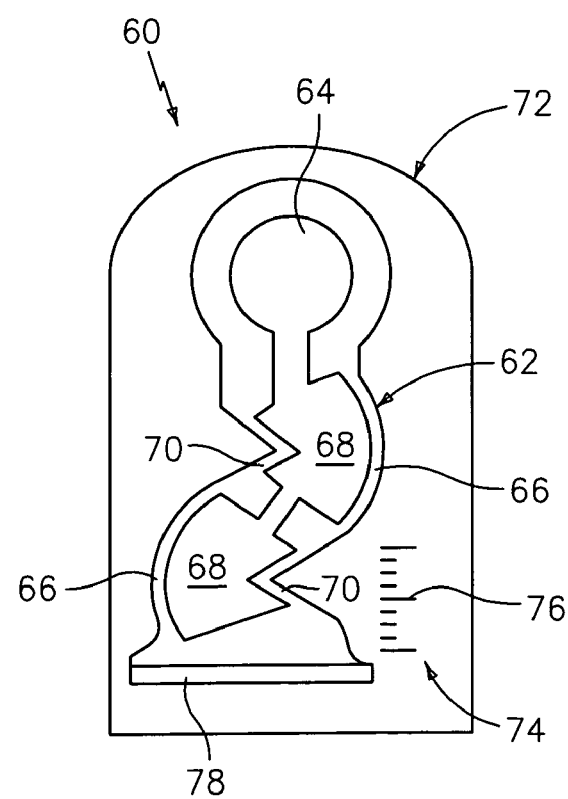
FIG. 5 depicts an inflatable manometer in an alternate embodiment of the invention.

FIG. 5 depicts another manometer 60 in an alternate embodiment. Manometer 60 includes an air cell 62 and a fluid inlet 64. The manometer 60 indicates pressure of the fluid which may be gas, liquid, etc. The air cell 62 is formed by two sheets of material sealed along edges 66. The shape of seal 66 defines a number of sub-cells 68, each having a concavity 70. The sub-cells are in fluid communication with each other, and inlet 64. The concavity 70 in FIG. 5 is a triangular wedge, but it is understood that other geometries may be used. In one embodiment, the sheets of material defining air cell 62 are thermoplastic material and are sealed using known techniques such as heat sealing, ultrasonic welding, etc. The sheets of material are not limited to thermoplastic materials and may be implemented using any flexible material such as rubber, glued paper, etc.

Air cell 62 and inlet 64 may be positioned within a housing 72 having a first and second sheet sealed along the periphery encasing the air cell 62 and inlet 64. The first and second housing sheets may be thermoplastic material and are sealed using known techniques such as heat sealing, ultrasonic welding, etc. A scale 74 is also formed on the housing 72 and includes indicia 76 representative of pressure. The scale 74 and indicia 76 may be formed by molding the indicia 76 into thermoplastic sheets (e.g., heat stamping) or printing the indicia 76. The scale 74 is positioned proximate to a distal end 78 of air cell 62. The scale 74 can be designed for different real units of measure, e.g., PSI.

Figure 6:
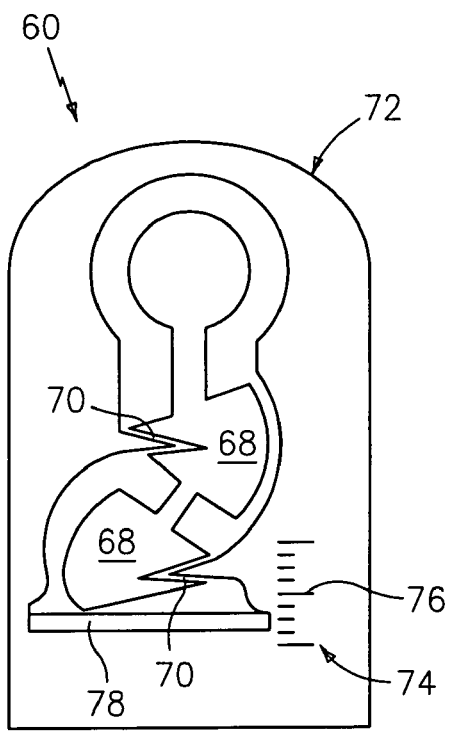
FIG. 6 depicts the manometer of FIG. 5 as pressure increases.

FIG. 6 depicts manometer 60 as pressure in air cell 62 increases. As the air cell 62 is inflated, sub-cells 68 contract at concavity 70, as described above with reference to FIG. 2, thereby reducing the length of the air cell 62 in a linear direction. The pressure within the air cell 62 is represented by the position of distal end 78 relative to scale 74. The distal end 78 of the air cell 62 may be colored to more easily determine the position of the end of the air cell 62 relative to the scale 74. Thus, the size and shape of the air cell 62 and scale 74 are designed to provide an accurate indication of pressure.

Figure 7A:
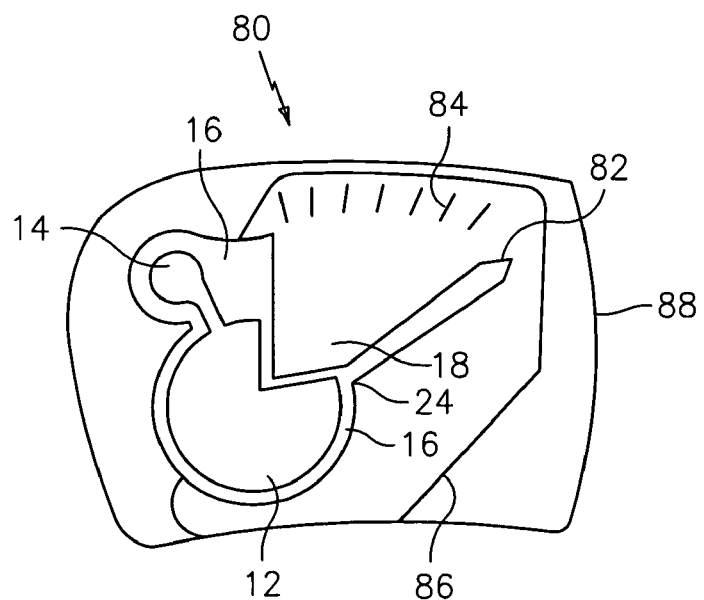
FIGS. 7A and 7B depict inflatable manometers in alternate embodiments of the invention.
Figure 7B:
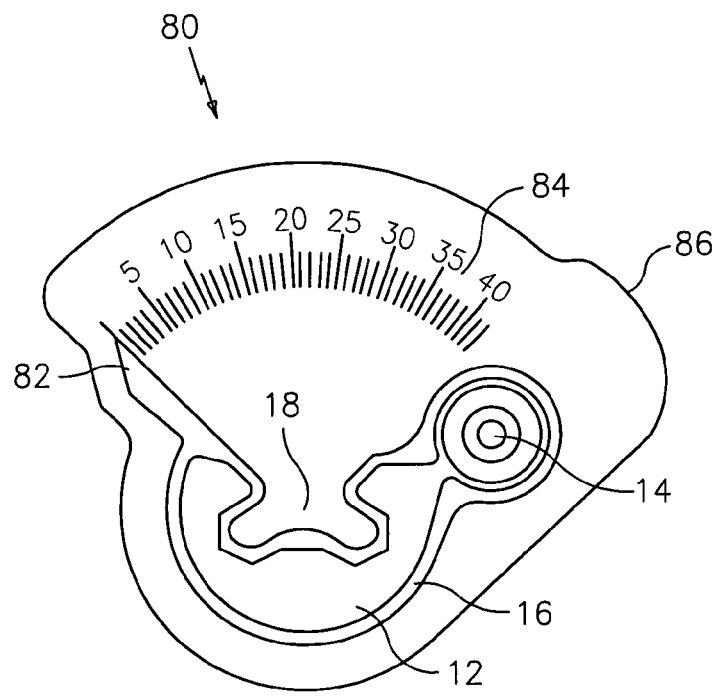

FIG. 7A depicts a manometer 80 in an alternate embodiment of the invention. Manometer 80 is similar to manometer 10 in FIG. 1A and similar components are labeled with the same reference numerals. Manometer 80 includes an indicator 82 extending from edge 24 of concavity 18. Rather than scale 20 formed in the sheet defining the air cell 12, manometer 80 includes a scale 84 printed on a separate card 86. The manometer 80 and the printed scale 84 may be encased within a transparent housing 88. The housing 88 includes an opening to access the fluid inlet 14 to the manometer 80. FIG. 7B depicts an alternate manometer similar to that shown in FIG. 7A, but having differently shaped concavity 18.

FIG. 8 depicts a manometer 90 in an alternate embodiment of the invention. The manometer 90 is formed from two sheets sealed together (e.g., thermoplastic sheets sealed together) to define an air cell 91 and an inlet 96 for fluid. The sheets of material are not limited to thermoplastic materials and may be implemented using any flexible material such as rubber, glued paper, etc. Inlet 96 is in fluid communication with a chamber for which pressure monitoring is desired. Manometer 90 includes two concavities 92 and 94, having differing characteristics. The concavities 92 and 94 have different widths so that each notch will close at different pressures. It is understood that other characteristics of concavities 92 and 94 may be varied including length, width and shape. The manometer 90 may also include a single concavity rather than two concavities. The single concavity may correspond to a minimum pressure that should be maintained or a maximum pressure that should be avoided. The distal end 98 of the manometer 90 may serve as a fluid outlet so that manometer 90 may be positioned inline in a pressure system to indicate pressure of a chamber connected to outlet 98.

FIG. 9 shows manometer 90 as pressure increases in air cell 91. As shown in FIG. 9, the opening of concavity 92 with the smaller width closes at a first predetermined pressure while concavity 94 has started to contract. Concavity 94 with the larger width has started to contract and closes at a second pressure. This allows an operator to determine that air cell 91 has been inflated to a pressure between two limits without requiring a scale indicating a numerical pressure value. Manometer 90 may be used in a variety of applications including indicating pressure of pilot balloons associated with tracheal devices.

The inlet in the manometers of FIGS. 1–9 may be eliminated and the air cell pressurized with a fluid and sealed. In this embodiment, the manometer indicates ambient pressure in response to a difference between ambient pressure and pressure in the air cell.

Figure 10:
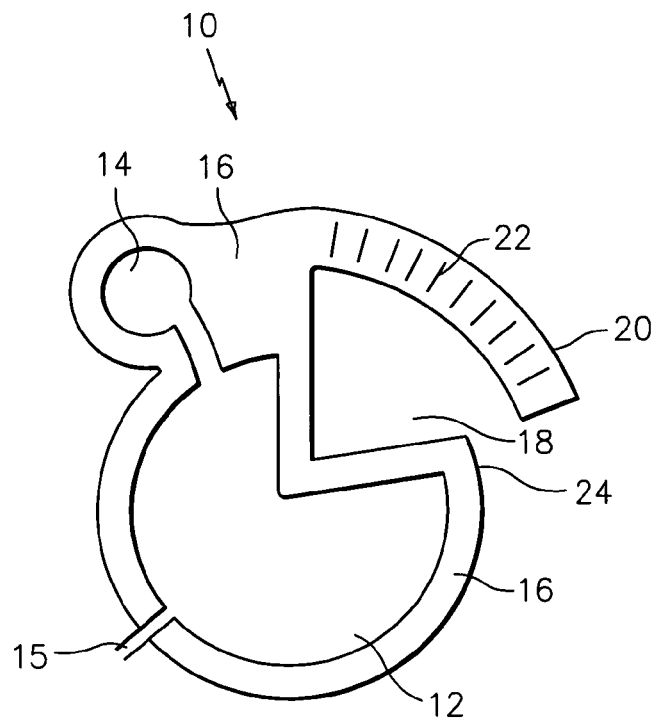
FIG. 10 depicts an inflatable manometer in an alternate embodiment of the invention.

FIG. 10 depicts an inflatable manometer in an alternate embodiment of the invention. The manometer 10 is similar to that shown in FIG. 1 and includes an outlet 15 in air cell 12. In this embodiment, the manometer 10 serves as a flowmeter to indicate a pressure differential between inlet 14 and outlet 15. In this configuration, the manometer may be used to indicate positive pressure, negative pressure or fluid flow. As long as the pressure within the manometer chamber 12 is positive to inflate the chamber 12 and cause edge 24 to move relative to scale 20.

While the invention has been described with reference to exemplary embodiments, it will be understood by those skilled in the art that various changes may be made and equivalents may be substituted for elements thereof without departing from the essential scope thereof. Therefore, it is intended that the invention not be limited to the particular embodiments disclosed for carrying out the invention, but that the invention will include all embodiments falling within the scope of the appended claims.

What is claimed is:

1. An inflatable manometer comprising:
   an air cell having a concavity formed therein, said concavity having two edges, wherein increased pressure within said air cell causes contraction of said concavity moving said two edges towards each other a scale positioned proximate to said air cell, a position of said air cell relative to said scale being indicative of pressure within the air cell.

2. The inflatable manometer of claim 1 wherein:
   one edge of said edges moves relative to said scale in response to pressure in said air cell, the position of said edge relative to said scale being indicate of pressure.

3. The inflatable manometer of claim 1 wherein:
   said scale and said air cell are integrally formed in thermoplastic material.

4. The inflatable manometer of claim 1 wherein:
said air cell is a circular air cell and said concavity is a section removed from said circular air cell.

5. The inflatable manometer of claim 1 wherein:
said air cell includes a plurality of sub-cells in fluid communication, each sub-cell including a concavity, wherein increased pressure within said air cell causes contraction of said air cell in a linear or radial direction.

6. The inflatable manometer of claim 5 further comprising:
a housing containing said air cell, said scale being positioned on said housing.

7. The inflatable manometer of claim 5 wherein:
a distal end of said air cell is colored.

8. The inflatable manometer of claim 5 wherein:
each sub-cell is rectangular.

9. The inflatable manometer of claim 5 wherein:
each sub-cell is semi-circular.

10. The inflatable manometer of claim 1 wherein:
said scale is printed on a card.

11. The inflatable manometer of claim 10 further comprising:
an indicator coupled to said manometer, said indicator moving relative to said scale in response to changes in pressure in said air cell.

12. The inflatable manometer of claim 1 further comprising:
a second concavity formed in said air cell, said concavity having a first characteristic such that said concavity closes at a first pressure, said second concavity having a second characteristic such that said second concavity closes at a second pressure, said second pressure being greater than said first pressure.

13. The inflatable manometer of claim 12 wherein:
said first characteristic is width and said second characteristic is width.

14. The inflatable manometer of claim 1 further comprising:
a fluid inlet and a fluid outlet coupled to said air cell, said manometer indicating a pressure differential between said fluid inlet and said fluid outlet.

15. The inflatable manometer of claim 14 wherein:
said fluid inlet and said air cell are formed from thermoplastic sheets sealed to define said fluid inlet and said air cell.

* * * * *